(12) United States Patent
Toia

(10) Patent No.: US 6,351,858 B1
(45) Date of Patent: Mar. 5, 2002

(54) PROCESS FOR DISPOSING OF HUMAN WASTES, A DISPOSABLE CONTAINER FOR COLLECTING HUMAN WASTES AND A CONTAINER-GRINDING MACHINE

(76) Inventor: Mario Fernando Toia, Republica Arabe Siria 3160, 8th Fl. "D", 1425 Buenos Aires (AR)

( * ) Notice: Subject to any disclaimer, the term of this patent is extended or adjusted under 35 U.S.C. 154(b) by 0 days.

(21) Appl. No.: 09/536,709

(22) Filed: Mar. 28, 2000

Related U.S. Application Data

(63) Continuation-in-part of application No. 09/178,683, filed on Oct. 26, 1998, now abandoned.

(30) Foreign Application Priority Data

Nov. 18, 1997 (AR) .......................................... 970105376
Oct. 8, 1998 (AR) .......................................... 980105027

(51) Int. Cl.[7] ................................................ A61G 9/00
(52) U.S. Cl. ............................... 4/450; 4/757; 220/4.01; 220/752
(58) Field of Search .......................... 4/450, 451, 452, 4/456, 457; 220/4.01, 752

(56) References Cited

U.S. PATENT DOCUMENTS

| | | | | |
|---|---|---|---|---|
| 412,734 A | * | 10/1889 | Drahos ........................... | 4/450 |
| 892,324 A | | 6/1908 | Staudinger | |
| 1,368,874 A | * | 2/1921 | Zender ........................... | 4/450 |
| 2,188,844 A | * | 1/1940 | Pedersen ........................ | 4/456 |
| 2,195,156 A | * | 3/1940 | Steward ......................... | 4/445 |
| 2,611,903 A | * | 9/1952 | Wakeman ....................... | 4/450 |
| 3,212,107 A | * | 10/1965 | Meltiou .......................... | 4/450 |
| 3,306,515 A | | 2/1967 | Beaumont | |
| 3,460,164 A | * | 8/1969 | Patton ............................ | 4/451 |
| 3,503,080 A | * | 3/1970 | Laufer et al. ................... | 4/451 |
| 3,599,249 A | | 8/1971 | Reed | |
| 3,840,906 A | * | 10/1974 | Huggins ......................... | 4/451 |
| 3,846,849 A | * | 11/1974 | Dooley et al. .................. | 4/450 |
| 3,848,274 A | * | 11/1974 | Oliver ............................ | 4/456 |
| 3,927,426 A | | 12/1975 | Geddes | |
| 3,962,732 A | | 6/1976 | Mills | |
| D253,304 S | | 10/1979 | Nakao et al. | |
| 4,448,313 A | | 5/1984 | Pomeroy et al. | |
| 4,696,067 A | | 9/1987 | Woodard | |
| 5,110,525 A | * | 5/1992 | Kolsky et al. ............... | 264/122 |
| 5,136,733 A | * | 8/1992 | Church .......................... | 4/456 |
| 5,697,921 A | * | 12/1997 | Blair ........................... | 604/317 |
| 5,819,334 A | * | 10/1998 | Maze ............................. | 4/450 |

FOREIGN PATENT DOCUMENTS

| | | |
|---|---|---|
| GB | 2 019 209 A | 10/1979 |
| GB | 2 108 381 A | 5/1983 |

* cited by examiner

*Primary Examiner*—Stephen P. Garbe
*Assistant Examiner*—Joseph C. Merek
(74) *Attorney, Agent, or Firm*—Crowell & Moring, LLP

(57) ABSTRACT

A process for disposing of human wastes in an efficient and environmentally or pathologically safe manner, a grindable container for collecting human wastes and a crushing machine for said containers. The container is made of a grindable, biodegradable material such as cellulose pulp and is designed to hold human wastes without any leaks or cracks. The container is formed by an upper portion and a lower portion, both comprising corresponding snap-in peripheral engaging flanges for engaging one to the other without the use of gluing products and comprising a anti-slipping surface finish for avoiding slippage of the container during usage and designed for comfortable human skin contact. The crushing machine is designed to be used at any health-care or rest-home center and is adequate for dumping the final product into a sewer system in an environmental caring manner.

8 Claims, 14 Drawing Sheets

FIG. 7A
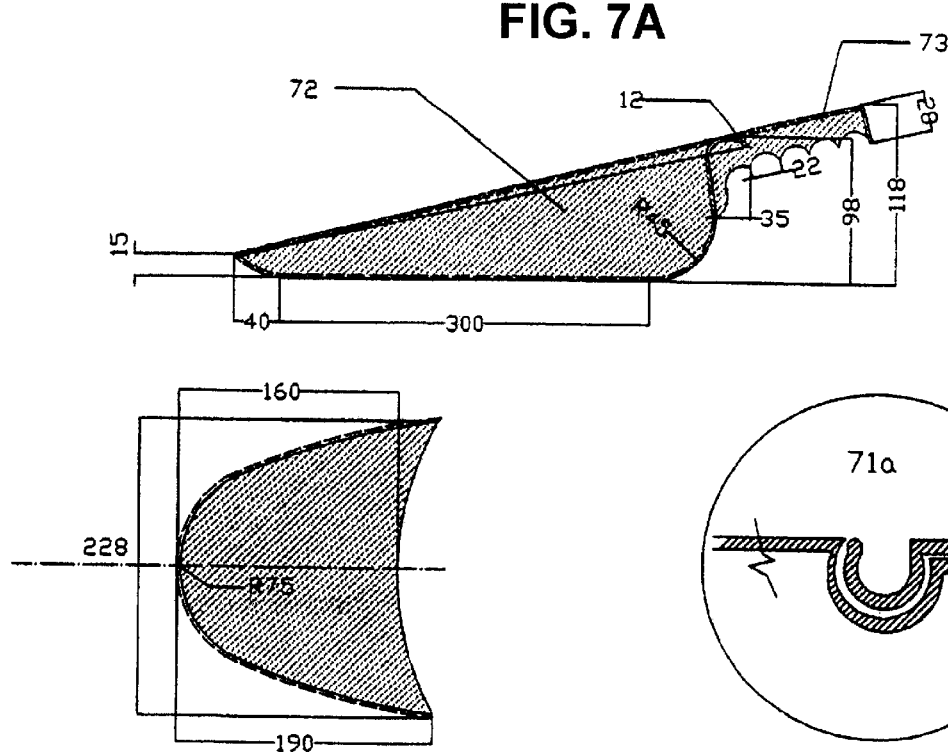
FIG. 7B
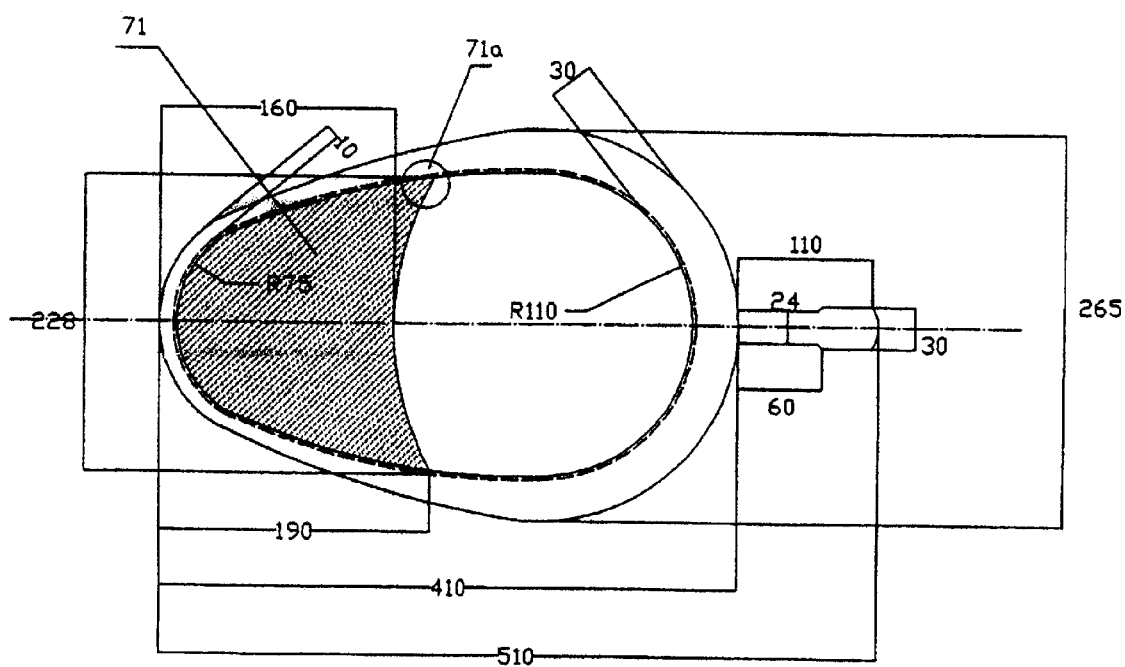
FIG. 7C

| t[min.] | 0 | 1 | 2 | 3 | 4 | 5 | 6 | 7 | 8 | 9 | 10 | 15 | 20 | 25 |
|---|---|---|---|---|---|---|---|---|---|---|---|---|---|---|
| T[°C] | 60 | 54 | 48 | 43 | 40 | 37 | 35 | 32 | 30 | 29.5 | 28.5 | 24 | 22 | 21.5 |

| t[min.] | 0 | 1 | 2 | 3 | 4 | 5 | 6 | 7 | 8 | 9 | 10 | 15 |
|---|---|---|---|---|---|---|---|---|---|---|---|---|
| T[°C] | 43 | 36 | 33 | 32 | 31 | 30 | 30 | 29 | 28 | 27 | 26.5 | 24 |

| t[min.] | 0 | 1 | 2 | 3 | 4 | 5 | 6 | 7 | 8 | 9 | 10 |
|---|---|---|---|---|---|---|---|---|---|---|---|
| T[°C] | 70 | 62 | 57 | 51 | 41 | 37 | 34 | 31 | 29 | 27 | 25 |

| t[min.] | 0 | 1 | 2 | 3 | 4 | 5 | 6 | 7 | 8 | 9 | 10 | 15 | 20 |
|---|---|---|---|---|---|---|---|---|---|---|---|---|---|
| T[°C] | 0 | 10 | 10.5 | 11 | 11.5 | 12 | 12.5 | 13 | 13.5 | 14 | 14.5 | 16 | 17 |

| T (MIN) | 0 | 1 | 2 | 3 | 4 | 5 | 6 | 7 | 8 | 9 | 10 | 15 | 20 | 25 |
|---|---|---|---|---|---|---|---|---|---|---|---|---|---|---|
| T (°C) | 60 | 54 | 48 | 43 | 40 | 37 | 35 | 32 | 30 | 29,5 | 28,5 | 24 | 22 | 21,5 |

| T (MIN) | 0 | 10 | 20 | 30 | 40 | 50 | 60 | 70 | 80 | 90 | 100 | 110 | 120 | 130 |
|---|---|---|---|---|---|---|---|---|---|---|---|---|---|---|
| T (°C) | 60 | 28,5 | 22 | 21,5 | 20,5 | 20 | 19 | 19 | 19 | 19 | 18,5 | 18,5 | 18 | 21,5 |

| T (MIN) | 0 | 20 | 40 | 60 | 80 | 100 | 120 | 140 | 160 | 180 | 200 | 220 | 240 | 260 |
|---|---|---|---|---|---|---|---|---|---|---|---|---|---|---|
| T (°C) | 60 | 22 | 20,5 | 19 | 19 | 18,5 | 18 | 18 | 18 | 18 | 17,7 | 17,7 | 17,5 | 17,3 |

PROCESS FOR DISPOSING OF HUMAN WASTES, A DISPOSABLE CONTAINER FOR COLLECTING HUMAN WASTES AND A CONTAINER-GRINDING MACHINE

This application is a continuation-in-part of application Ser. No. 09/178,683, filed Oct. 26, 1998 abandoned.

The present invention relates to a process for disposing of human wastes, a disposable container for collecting human wastes, a process for producing the disposable container and a container-grinding machine for disposing of the container.

The importance of the sanitary disposal of human wastes from health-care centers has been a constant issue in every community, and this importance keeps growing as long as hospitals and clinics tend to improve their health and prophylactic standards in view of the great prevalence of high-risk diseases.

The main interest of urban authorities is not only targeted to avoid sewerage system overloading, but also to guarantee that these are capable of delivering organic wastes without contaminating the environment, since they may represent a growth medium for contagious diseases and for insects that convey such diseases.

Known processes for collecting and recovering human wastes from health-care centers are limited to the use of plastic or metal containers, which are presumably easy to clean, for transferring wastes to a nearby collecting sewer-inlet. After being used, it is the responsibility of the hospital staff to appropriately clean and disinfect said containers. These procedures have proven to be ineffective and diseases spreading means throughout treatment centers and rest homes. It is apparent that this requirement has not been met because of the lack of elements that could overcome the above problems in an effective and cost effective manner.

DESCRIPTION OF THE RELATED PRIOR ART

Several urinals and containers for collecting human wastes are known in the art.

U.S. Pat. No. 4,696,067 (Woodward) describes an open box urinal which comprises flexible walls and a relatively stiff bottom, to be used by pressing the walls together with the user's thighs in order to hold the container in place without other support during use. However, the document does not mention nor suggests a container for collecting solid human feces, menstrual fluids or any other organic material other that urine, as is described in the embodiment of FIGS. 7A and 7B of the present invention. In column 1, lines 9–17, lines 31–39, and in the preamble of claim 1 the cited document makes it clear that the urinal is designed to be used by a female user, whilst the present invention is by no means restricted in that sense and may be used by both men or women, children or elderly people, being only restricted by a maximum weight of approximately 330 lbs. In column 1, lines 55–58 the cited document mentions that the urinal was designed for erect urination in order to keep the patient's vulva clean. However, the embodiment of FIGS. 7A and 7B of the present invention is designed with a structural profile to be used with patients that are either unable to get off their bed, or are asleep or are unable to consciously collaborate with the nurse, being particularly adequate for being shifted under the patient while lying down. The urinal described by Woodward would be totally inadequate for this usage. In column 2, lines 60–63 the cited document discloses a box made of resiliently flexible plastic. This totally deviates from the present invention's concept in the sense that the latter claims a disposable, substantially biodegradable material, comprising cellulose pulp or cellulose-derived material, such as cardboard or similar. The material described in the cited document is not biodegradable and would be totally inadequate for disposing and grinding as described by the present invention. Finally Woodward defines an open box with flexible walls to be deformed by a female user's thighs whilst the embodiment of FIGS. 7A and 7B of the present invention is designed with a certain profile and includes a lid that contributes to keep its original shape provided the maximum user's weight of approximately 330 lbs. is not exceeded. Finally this document does not mention or describe the fact that a container lid is designed and selected for acting as a structural reinforcement for attaining a overall resistance of up to 330 lbs, nor the fact that the lid has a texturized, anti-slipping surface for avoiding slippage during usage.

Patent GB 2,019,209 (Turner) describes a urinal which is expendable and intended to be destroyed after use, made of molded fiber pulp and formed by upper and lower portions having respective flanges which are glued together to form the complete urinal. The present invention shows an embodiment in FIGS. 7A and 7B for collecting human wastes and is not restricted to urine. This difference is supported by the design of the shape of this embodiment. Turner does not mention in any way the fact that the urinal may be shifted underneath a laying patient for collecting solid feces and the shape of his urinal is totally inadequate for doing so. Turner describes flanges that are glued together to form the complete urinal whilst the present invention claims a lower portion and an upper portion which are snapped together by means of a flange design that avoids the use of adhesives or glues. This is an important advantage since glues are products which may require the addition of bactericides that may cause allergies in patients with particularly sensible skin. Additional to this, the extra costs and stocking facilities needed for keeping enough glue or the stocking facilities needed for keeping previously glued assemblies are clear handicaps of the urinal described by Turner, and which are solved by the present invention. Turner does not mention any thickness that may attain the imperviousness during two hours or more and it does not mention or describe the fact that a container lid is designed and selected for acting as a structural reinforcement for attaining a overall resistance of up to 330 lbs, nor the fact that the lid has a texturized, anti-slipping surface for avoiding slippage during usage.

U.S. Pat. No. 3,927,426 (Geddes) describes a urinal made by blow molding process which may be used by both male and female patients thanks to a replaceable adapter that adapts anatomically to the different genital configurations, also including a closure or odor shield with a hinge portion which fits over the open end of the adapter for sealing the interior of the container. The base of the container is enlarged for better stability in an upright position. In column 2, line 40, Geddes describes the container as being a plastic blow molded container and does not mention or suggest any embodiment that may be made of a disposable, grindable or biodegradable material that may be dumped by means of a grinding machine into the sewer system. The present invention defines a container with a definite thickness range for assuring imperviousness of walls made of biodegradable material. Further, the cited document does not describe a urinal or a bedpot comprised by two portions which are engaged by snapping and free of gluing.

U.S. Pat. No. 3,599,249 (Reed) describes a disposable bedpan comprising a folded box of initially flat cardboard material and a separate waste- receiving tray of disposable material. Integral spaced-apart projections in the tray support the box at the desired contour under the weight of a patient. Each side of the box has a waste-receiving opening and the openings are of different sizes to permit reversal of the box with respect to the tray to accommodate either children or adult patients. Although the bedpan described by Reed seems to be adequate for holding waste for some time, no mention is made in the sense that the walls are made within a definite thickness range that may assure an imperviousness of approximately two hours or more. Further, the cited document does not describe a urinal or a bedpot comprised by two portions which are engaged by snapping and free of gluing. Reed describes an internal tray with spaced apart projections for attaining enough rigidity for a user to sit on it. However, in the present invention this is achieved by means of two different aspects: a) a shell-type lower portion with enough wall thickness and b) a specially designed lid which not only avoids spillage but also contributes in enhancing the stress distribution.

U.S. Pat. No. 3,306,515 ( Beaumont) reveals a disposable urinal formed from a flat, unitary sheet of an impermeable material. This document does not show a bedpan that may be used by a patient lying on a bed and unable to collaborate with the nurse and is not adequate for collecting solid human feces. The document does not mention that the container is capable of withstanding the weight of a patient and due to its overall profile, it is not adequate to be slipped under a lying patient.

U.S. Pat. No. 3,962,732 ( Mills) describes a disposable bedpan assembly formed by a bedpan and a optional support. Although the document describes a definite overall profile for letting the assembly be slipped under a patient, it does not mention any particular lid surface design for avoiding slippage of the container under the patient's weight when used.

It is therefore an overall object of this invention to overcome the problem of the lack of hygiene and asepsis of conventional human waste collection methods in health-care centers and rest homes.

OBJECTS OF THE INVENTION

It is an object of the present invention to provide a process for collecting and transporting human wastes in a sanitary and safe manner, without involving the contact of personnel with these wastes, enclosing them in a disposable container, for the purpose of processing said container in a grinding machine and discharging the resulting fluid into the sewer-pipe.

It is another object of the present invention to provide a disposable, grindable, and substantially biodegradable container that is useful to carry out said process.

(It is a further object of the present invention to provide a disposable, grindable, container that is built of a substantially non-biodegradable material and useful to carry out said process).

(It is a further object of the present invention to provide a sterile and packaged container, which is disposable, grindable, and substantially biodegradable, and useful to carry out the above process).

(It is a further object of the present invention to provide a sterile and packaged container, which is disposable, grindable, and built of a substantially non-biodegradable material, that is useful to carry out said process).

(It is another object of the present invention to provide a grinding machine or crushing mill to carry out the above process.)

It is a still further object of the present invention to provide a process of manufacturing the disposable container.

DESCRIPTION OF THE DRAWINGS

FIG. 7A is a left side view of the disposable container embodiment in the shape of a flat bed-pot with its corresponding snap-in lid FIG. 7B shows a detail of the front portion as seen in a plan view and a detailed view of the lid snap-in engagement flange of FIG. 7C.

FIG. 7C is a plan view of the disposable container embodiment in the shape of a flat bed-pot, including the snap-in lid.

DESCRIPTION OF THE PREFERRED EMBODIMENT

The present invention refers to a process for disposing of wastes from people that are unable to care for themselves, whether it comprises feces, urine, menstrual fluids or any other organic material emitted by human beings, which require a safe handling and guaranteed disinfection. It also relates to the collection container employed and to the grinding or crushing machine used to crush said container. The method shown in FIG. 1 relies on the use of collection containers such as flat bed pots, urinals for male patients, etc., that are made of a disposable, grindable and preferably substantially biodegradable material which does not contaminate the environment when being delivered to its final destination. When mentioning the disposable character of the material it is meant that it is a very low cost material. This will allow for the advantage of using it only once, which insures the complete sanitation of the process. This latter condition will lead the person responsible for cleaning the health care center to dispose of the container after it has been used, and said person will not even consider the possibility of reusing said container, because that will not bring about any economic profit, thus insuring the appropriate performance of the sanitary procedure, even in those places where there are no systematic means of control over the personnel.

In a highly preferred embodiment, the material comprising said disposable, grindable and substantially biodegradable container is cellulose pulp. In an alternative embodiment, the material proposed comprises any other cellulose-derived product, since these are grindable and low cost materials, e.g. cardboard, cork-like agglomerate, etc. (These are alternative materials since they are not considered substantially biodegradable).

The process for collecting human wastes in sanitary containers that are built of a disposable material insures the use thereof by only one person and only once. Such collection containers are lighter and easier to handle by users on account of the material they are made of and, in every case, the material the disposable containers are built of will be grindable, i.e., it will be capable of being crushed.

Process for Manufacturing Disposable Containers

The process for manufacturing the above containers (will depend on the selected material and does not pertain to this invention) is known in the art and is based on (as) a process for forming cellulose pulp or other cellulose-derived materials (into such containers). In the instance of the preferred embodiment, wherein the material chosen comprises cellulose pulp, FIGS. 4 and 5 show a process for manufacturing molded pulp.

Figure 4:
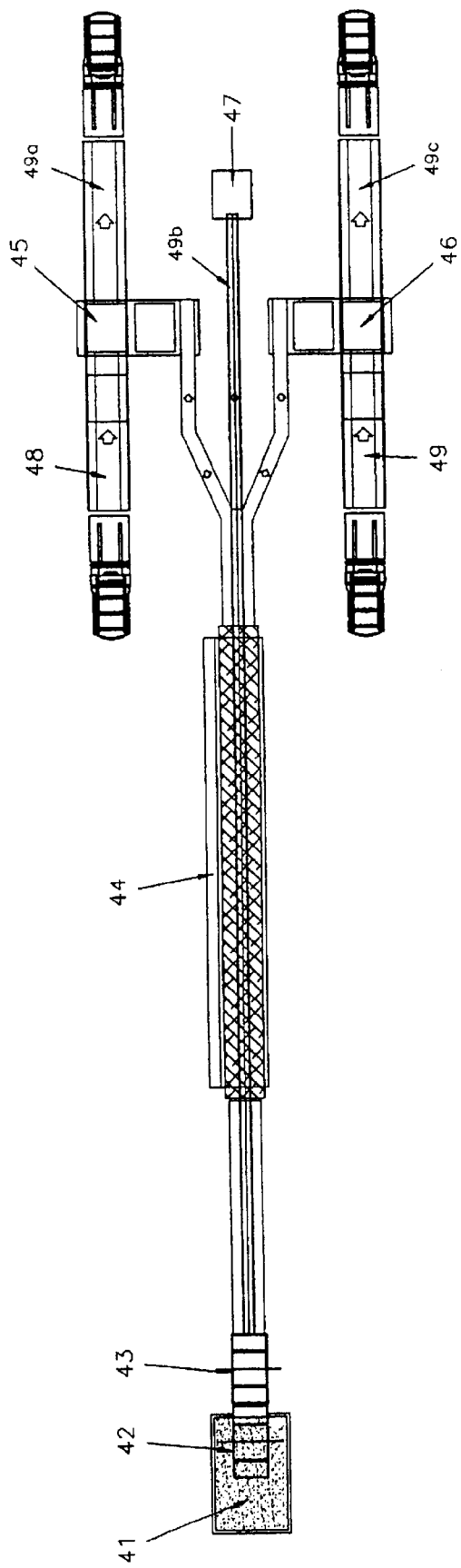
FIG. 4 is a plan view that shows the location of the pieces of equipment used in the first step of the process for making disposable containers, in a pulp embodiment.

The reference numbers in FIG. 4 are:
41. Paste bat
42. First roller
43. Second roller
44. Dryer oven
45. Lower portion palletizer or containers themselves
46. Lid palletizer
47. Handle collector.
48. Flat-link chain feeder of lower portion holders (stackable).
49. Flat-link chain feeder of lid holders (stackable)
49A. Lower portion holder conveyor.
49B. Handle conveyor belt.
49C. Lid holder conveyor belt.

FIG. 4 shows a primary production line assembly into which the cellulose pulp enters and which provides the three main portions of the disposable container: the lower portion of the container or container itself, the handle and the lid.
The references in FIG. 5 are:
51. Conveyor for the lower portions of the container.
52. Depalletizer for the container lower portions.
53. Empty container conveyor.
54. Lid holder conveyor.
55. Lid depalletizer.
56. Empty container conveyor.
57. Assembly-binding device for binding lower portions to their lids.
58. Handle positioning device.
59. Scented pad inserting device.
59A. Inkjet decoder.
59B. Packaging station.
59C Empty pallet feeder.
59D. Case packaging - palletizing device
59E. Conveyor for pallets with cases.

Figure 5:
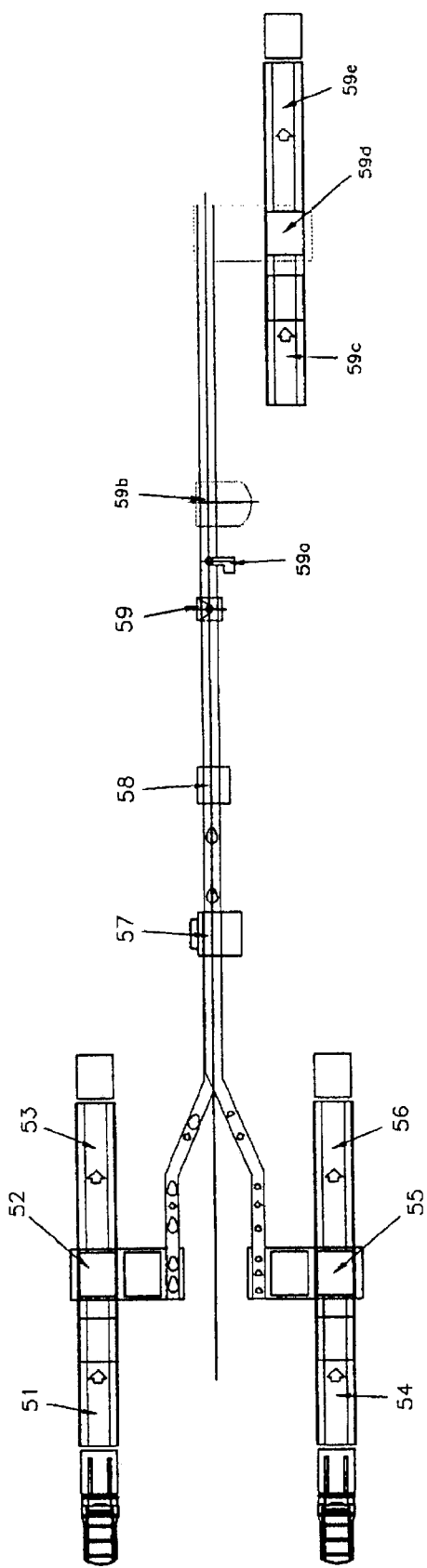
FIG. 5 is a plan view that shows the location of the pieces of equipment used in the second step of the process for making disposable containers, in a pulp embodiment.

FIG. 5 shows a secondary production line assembly into which the three members from the line disclosed in FIG. 4 will enter, said members exiting as fully assembled and packaged containers. FIG. 5 shows an (adhesive-laying and) assembling machine for binding the lower portions to their respective lids by means of glue-free snapping engagement. It is a pneumatic device that receives container lids from a delivery means fed by a lid holder through a conveyor belt and a feeding hopper Thereafter, and upon retention of the lower part of the disposable container itself, coming from a parallel line fed by container holders, the lid of the container, which has previously been provided with a biodegradable adhesive, is placed on the lower container and assembled onto it.) This machine is part of an alternative step of the process used for delivering the present invention to health facilities which prefer receiving the lower and upper container portions already assembled in a single unit.

In the same FIG. 5 a handle-inserting device is shown. Handles are fed through a vibrating/turning hopper, which arranges the position of the handles by placing them so that they move downward in a descent hopper that is registered with the feeding line. The adhesive-laying and final placing of the handle is carried out by means of an electro-pneumatic device driven by a PLC (programmable loop controller).

It is important to point out that, in a highly preferred embodiment, the disposable container is delivered packed into a sealed polyethylene or polypropylene bag, so as to keep its asepsis and sterilization, before being used.

In the step of baking the pulp, the temperature to which the material is subjected is 130° C., whereby any bacteria present therein, as well as other contaminating agents, are destroyed. Thereafter, being a target to maintain the asepsis of the container until it is bagged for delivery, the whole production line is installed within a cleanness-control chamber, in accordance with "clean room" techniques, so as to achieve a "gray" area scoring, with a particle count of less than 10 $\mu$g/m3, using the pollution measuring standards according to ANSI/ASHRAE 62—1989. The packaging of the resulting disposable container is carried out into the polyethylene or polypropylene bags in a final step before they leave the enclosure. The bagged assemblies are then irradiated with UV light to insure their asepsis during storage prior to use, and bags are heat-sealed after the containers are placed therein.

Molding of the Container

The steps and machinery for manufacturing a cellulose pulp-based product are well known in the art. However, the need for obtaining a comfortable anti-slippage finish on the container's surface requires the use of a particular molding technique which will be described.

The wet end of the molding machine consists of a series of wire mesh screen-covered wet forming dies mounted on a vacuum molding drum, and a matching set of transfer dies mounted on a transfer mechanism. The forming die is made up of rigid corrosive-resistant metal and usually consists of many component parts that are drilled with small drainage holes and covered by preformed stainless steel screens.

The forming dies, mounted on the molding drum, are rotated at a uniform speed and immersed in a vat containing the pulp slurry at about 0.75% per weight of fiber contained in recycled water. The pulp stock moves through the taper row vat in the same direction, and at approximately the same speed as the dies, in order to reduce fiber wash-off. A vacuum system attracts the fibers for depositing on the forming die screens as the suspending recycled water is drawn through the screen and drainage holes so that the fibers may orient themselves in a mechanically interlocked layer to form the molded fiber container. The water is recycled through the dose system for serving as dilution water for producing the mentioned 0.75% fiber contents at the recirculating vat and is further mixed at the pulper with waste paper for forming more pulp supply. When the mating transfer dies are accurately brought into contact wit the freshly formed fiber products, a gentle air puff coming from the forming die and a vacuum in the transfer die occur, the latter gently lifting off and transferring the delicate wet molded products onto the transfer die assembly.

The transfer die assembly consists of a series of transfer dies which rotate about a central shaft and are mounted on a series of pivot shafts. These pivot shafts are designed for locating, orienting and mating the transfer dies in precise synchronization with the movement of the wet forming dies, and for removing and transferring the weak wet molded products by vacuum at extremely high speeds and then depositing them on dryer conveyor trays by an alternate gentle air puff through the transfer dies when they are placed on the dryer conveyor. The transfer dies show air and vacuum holes and are made of urethane cast onto a machined bronze backing and are designed for providing optimum operation and durability.

The particular forming meshes used in cellulose molding are the clue for obtaining the a comfortable anti-slippage texturized surface required in these health care containers. When the molding process is being carried out, the mesh comes in tight contact with the cellulose fibers, and create the base on which these will deposit in order to follow the mold's profile. The molding mesh is made of a preferably corrosion resistant metal wire ( stainless steel, bronze, or the like) and are usually obtained in commercially standard grids classified by mesh openness ( so called "mesh grade", usually #50 or #60 for these applications). When molding with different mesh grades, different texturized surface finishes may be obtained and, when combining different mesh grades with different wire gauges, different anti-slippage surface designs may be obtained, regardless of the container's profile. The texturized anti-slippage surface finish is particularly comfortable for contacting human skin since it offers a grid-type smooth and soft finish which will not leave any pressure marks on the patient's skin, even if the contacting skin is scared or irritated.

Detailed Description of the Process of the Invention

The process of the invention is based on a sequence of steps that must be strictly pursued in order to insure the sanitary status of the facility in which it is carried out.

It is worth stating that the process relies on simple grinding and liquefying devices through which a homogeneous and liquid mass is obtained as an end product, which allows for its transfer into the sewer system.

Figure 1:
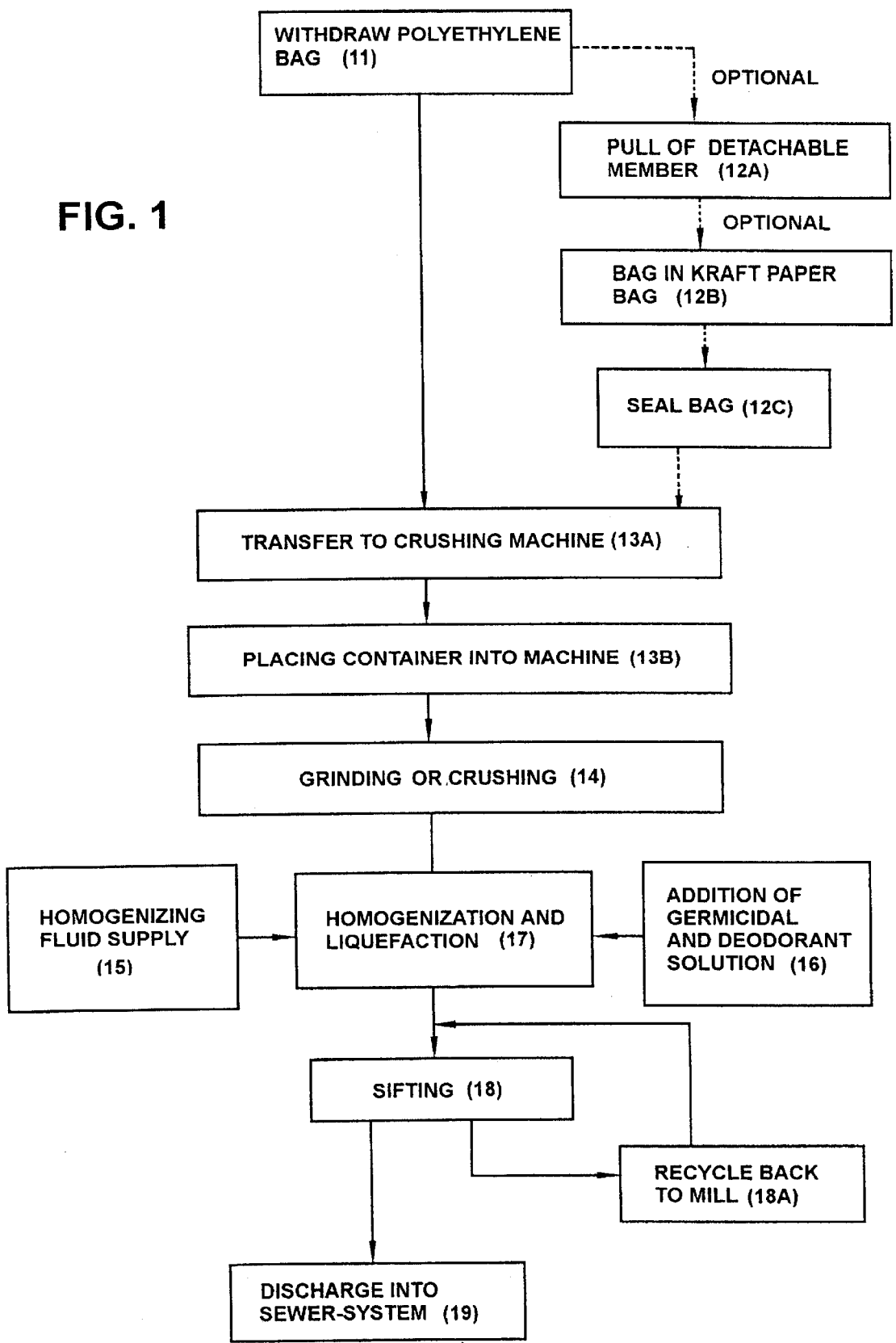
FIG. 1 shows a flow chart of the process as disclosed in the present invention.

The process in FIG. 1 starts with a step comprising withdrawing (11) the container out of the polyethylene, polypropylene or other similar materials, prior to use, which is then disposed of in a conventional manner that does not pertain to the process of the invention. Thereafter, the collection of human wastes is effected (12) into the disposable container in a conventional manner. In an optional embodiment, which involves the use of detachable handles or detachable, framed handle assemblies, an optional step (12A) of detaching said optional additional members is considered after the collecting step (12). In a further preferred embodiment. After that, a further step of bagging (12B) the container is performed by putting the container with its waste contents into a Kraft-type-type paper disposable bag that is provided with a coated inner side to make it impervious to splashes or spills, and closing the open end so as to prevent unpleasant odors to spread out into the environment. In any of the bag-sealing procedures, an element for preserving the biodegradability of the assembly is used. In a preferred embodiment, a glued area with a biodegradable adhesive is used, or else the operator may alternatively use a cotton string to strangle the open end of the bag. The string should be made of cotton so as to keep the overall biodegradability of the product.

The container is then transferred (13A) together with its contents, with or without a Kraft-type paper bag, to a grinding machine or a roller and blade mill. The time it takes to transfer a disposable container to the grinding machine should be less than 2 hours, being this time dependable on the number of grinding machines available in the building. For example, if the boarding floor of a hospital or clinic has a considerable number of wards (over 15), it is desirable to have at least one crushing equipment in every floor and a transferring cart per floor. However, the optimum number of grinding machines and transferring carts required per floor will vary according to the average number of hospitalized people with ambulatory impairments or difficulties.

The disposable containers are then delivered (13B) into the machine through the inlet thereof and are subjected to milling or grinding (14) by the mentioned rollers. At the inlet there is a perforated pipe (14), which supplies homogenizing fluid, preferably water, from several nozzles suitably arranged so as to help each disposable container slip into the grinding area, lubricate the milling operation and wash the feeding duct.

In the next step, proceeding with the flow chart in FIG. 1, after the disposable container is ground or crushed (14), the homogenizing and liquefaction step begins (17) through a cut and stir effect provided by high speed spinning of rotating blades. The entire mass of the material comprising the end product of this process is then sifted (18) by forcing the mass to pass through a mesh or sieve to prevent big residues from being pushed on to the following step. The sifted fragments fall by gravity into the lower area wherefrom the resulting fluid is discharged (19) into the sewer system, preferably by gravity and alternatively by means of a sewage pump.

At the time the mill is started, a spray-nozzle (atomizer) adds a germicide-deodorant solution to the product (15). In a preferred embodiment this solution is bleach (sodium hypoclorite). In alternative embodiments, other solutions may be used, such as concentrated sodium hypoclorite (commercially available as "liquid chlorine"), chloroxylenol parachlorometoxylenol, chlorometaxylenol, quaternary ammonium compounds, or benzalkonium chloride.

The fluid that is added in the homogenizing fluid addition step of the homogenizing and liquefaction process (17) is preferably water, due to its low cost and ready supply. The volume added in every step of the process is about 10 liters ( aprox. 2.5 gallons), supplied from the water line of the building, wherefore a connection for the machine is provided with a water blocking-deblocking element, preferably a solenoid valve wired 110 VCA (60 Hz) or a motorized ball valve. The addition (16) of a dilute germicidal solution to the ground mass is effected from an ancillary vessel, preferably from an elevated "backpack" type reservoir, mounted on the outside of the device and continuously refilled from the tap-water feeding line through a known mechanical means comprising a valve and float. The germicidal solution is added to the reservoir water so as to insure that the entire crushed product is disinfected, to disinfect the inner members of the machine and avoid the growth of fungi and mold. The addition of the concentrated germicidal solution is carried out by means of a known inverted container drop by drop system commonly used in toilet reservoirs.

The crushing mill is enclosed in a soundproof chamber that preferably comprises a double wall covering filled with a soundproof material so as to minimize the noise resulting from the device, particularly in a residential or therapeutic recovering environment. Preferably, the soundproof material will comprise glass wool or expanded polyurethane in the shape of sheets with a thickness of preferably 0.75–1 inch , over the walls, the bottom and top sides of the chamber. The rest of the machine is made of parts and materials that are well known in the art.

Preferred Embodiment of the Disposable Container

FIG. 7 shows a preferred embodiment, wherein both the lid (71) and the handle (73) are integral parts of the lower portion (72) of the disposable container, and this embodiment requires about 200 to 300 g (0.440–0.660 lbs) of cellulose pulp or other alternative cellulose-derived material.

Alternative Embodiments of the Preferred Container

In other alternative embodiments, the handle is not a part of the container, its use being thus dictated by the requirements of the production line. In these instances, three alternative embodiments are envisioned:

A) Both the container and the lid are made of pulp and the handle comprises a detachable member (FIG. 8) that is detached in step (12A) of the process. In this optional embodiment the detachable handle may be made, e.g., of plastics, stainless steel, prepainted iron plate, aluminum, bakelite or ferrous or non-ferrous alloys.

Figure 8:
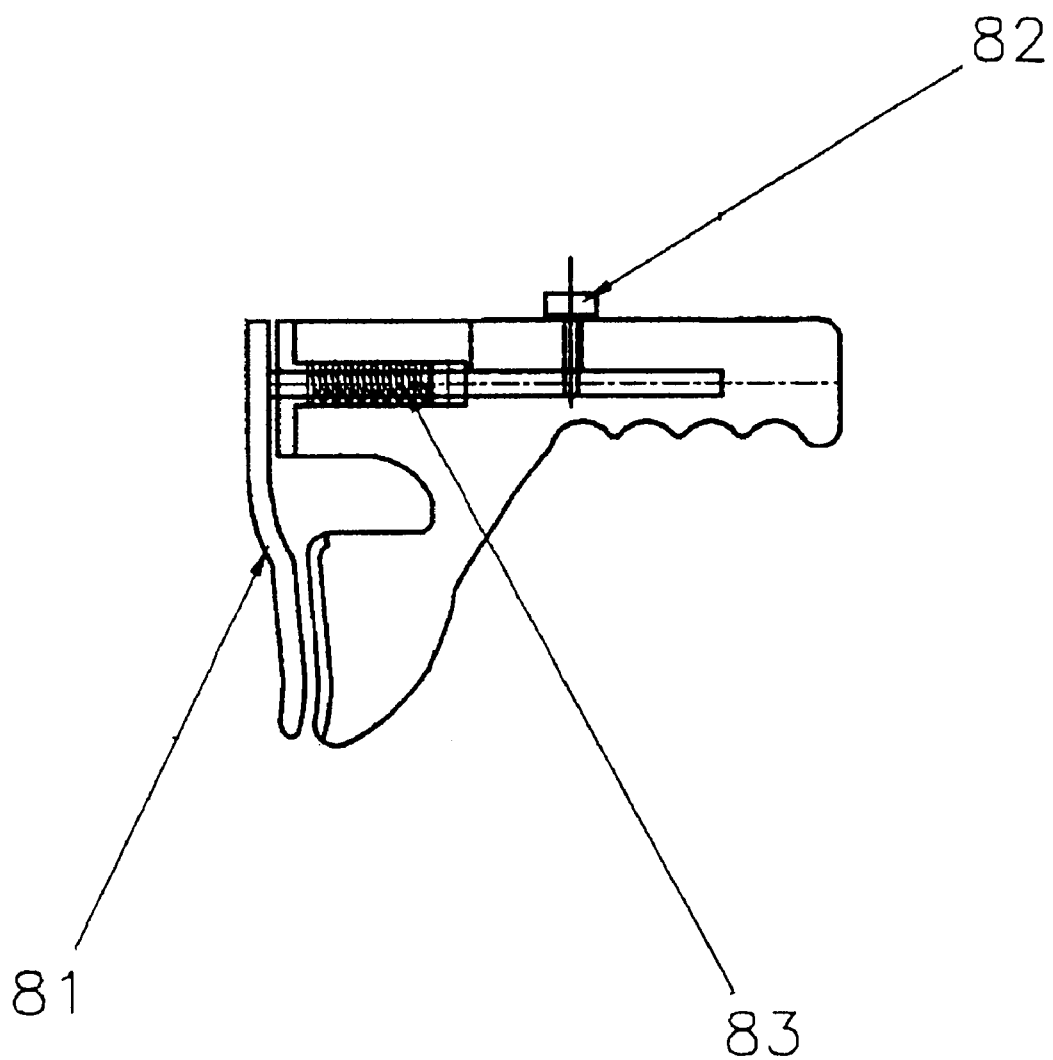
FIG. 8 is a side view of the alternative, non-disposable handle on a 1:2 scale.

FIG. 8 shows the following elements:
81. Expandable clamp
82. Driving cam for the expandable clamp.
83. Compression spring.

Figure 9A:
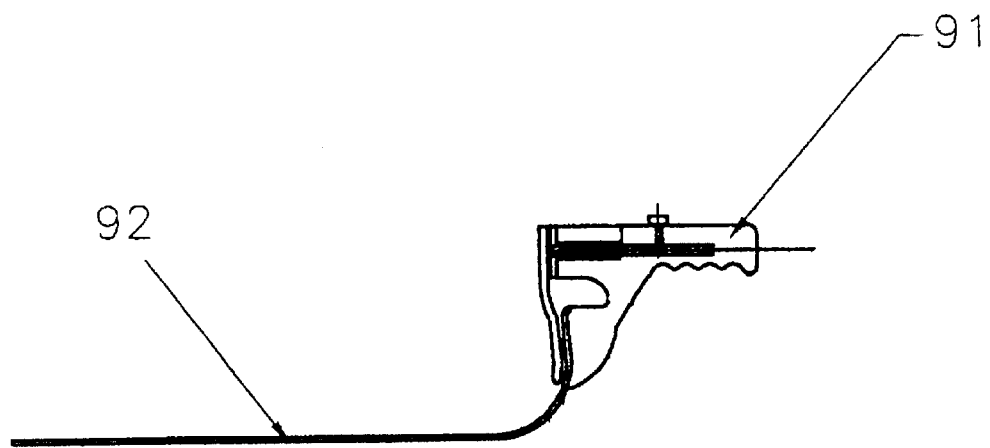
FIG. 9A is a side view of a framed, non-disposable handling device, on a 1:5 scale.
Figure 9B:
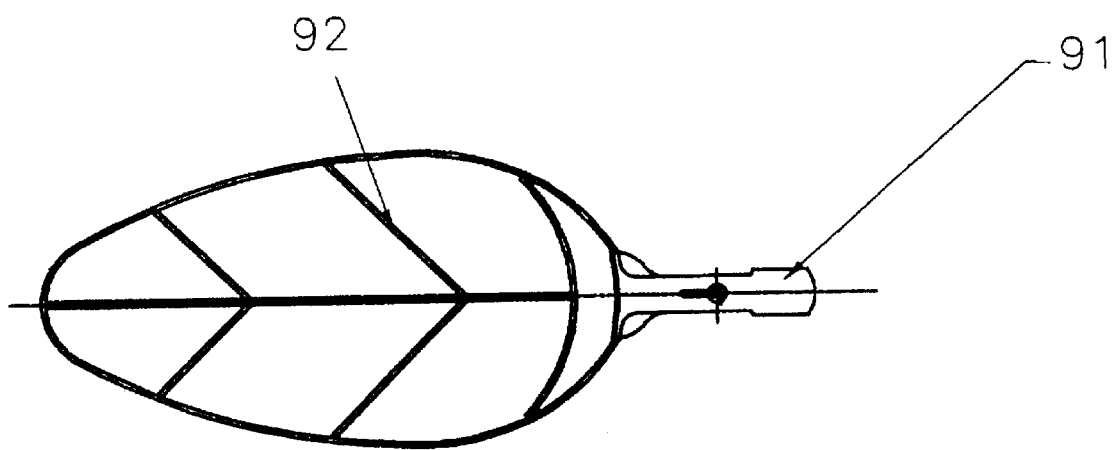
FIG. 9B is a plan view of a framed, non-disposable handling device, on a 1:5 scale.
Figure 10:
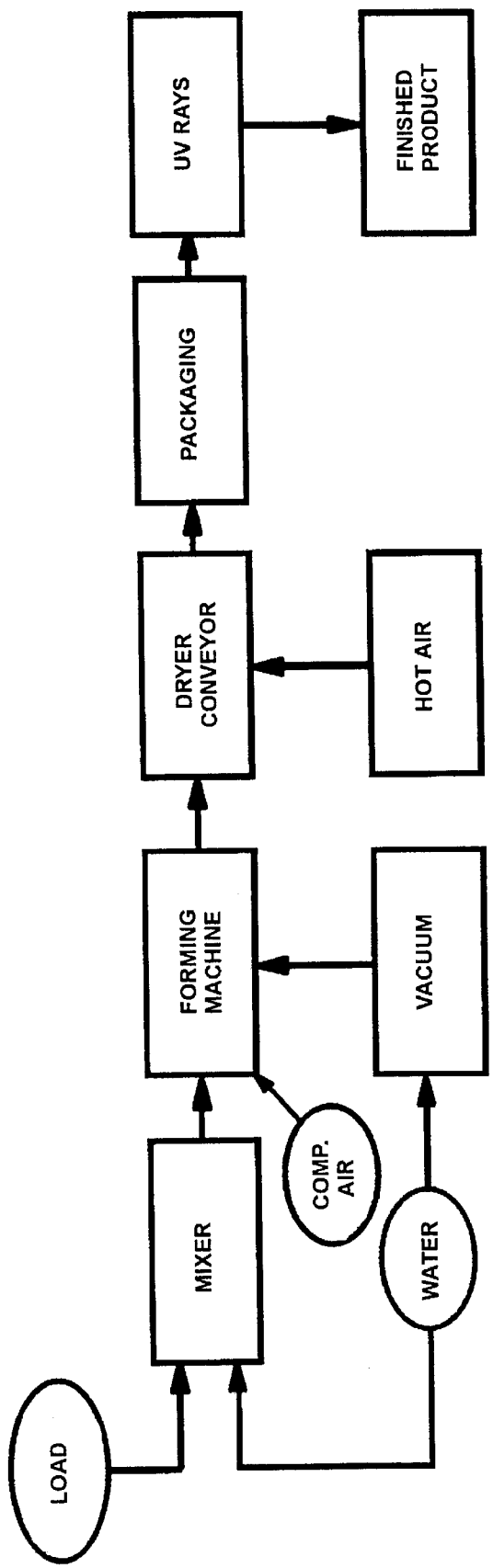
FIG. 10 shows the flow chart of process for manufacturing disposable containers in a pulp embodiment.

B) Identical to item (A) with the exception that the handle is a part of a handle-frame assembly (FIGS. 9A and 9B) that serves the purpose of handling the container for its transfer. The following elements are shown in FIGS. 9A and 9B:
91. Detachable handle.
92. support frame C) The use of other devices or pieces that are not part of the disposable container that might serve as handlers and are made of the same or different materials such as: plastic, stainless steel, pre-painted iron plate, aluminum, bakelite or ferrous or non-ferrous alloys.

According to the above, the elements described in items "A", "B" and "C" are reusable and must be detached (12A) from the disposable container before placing it in the Kraft-type paper bag. The use of these reusable elements may be desirable, since they allow to lower the cost of the forming process and a lesser amount of raw materials is required since they avoid the need to mold the handle.

Detailed Description of the Crushing Mill

Figure 3:
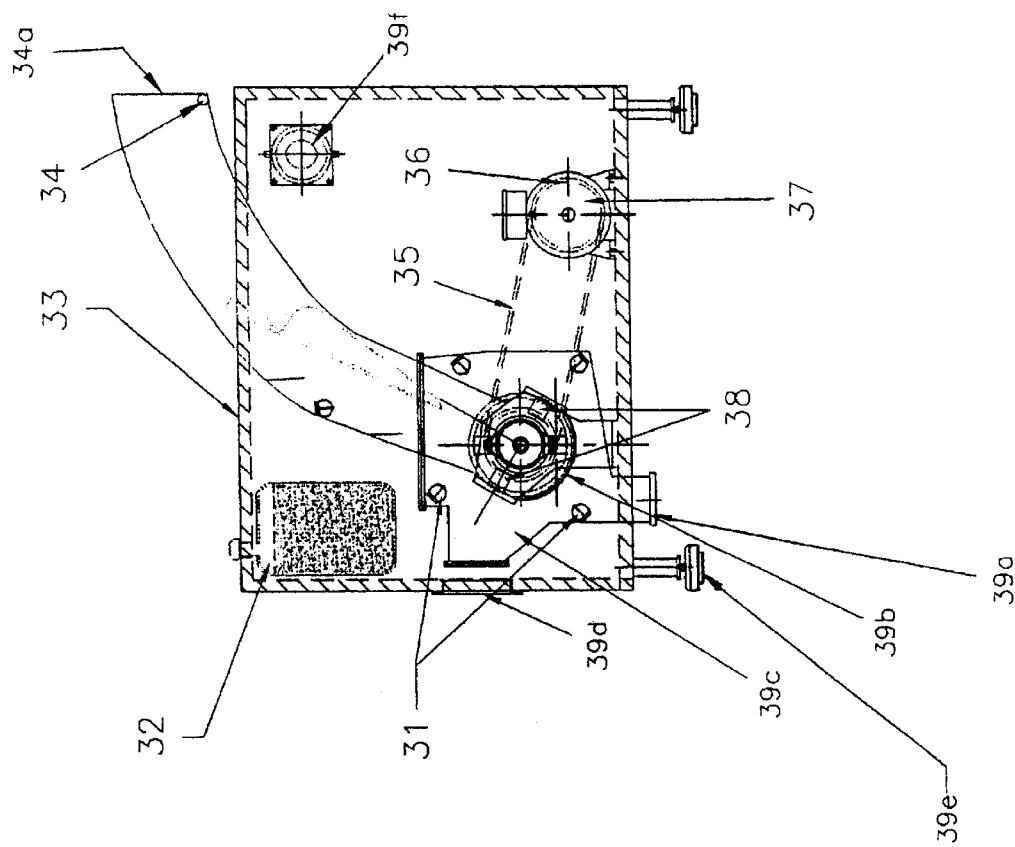
FIG. 3 shows a side view of the crushing mill used in the process of the present invention.
Figure 2:
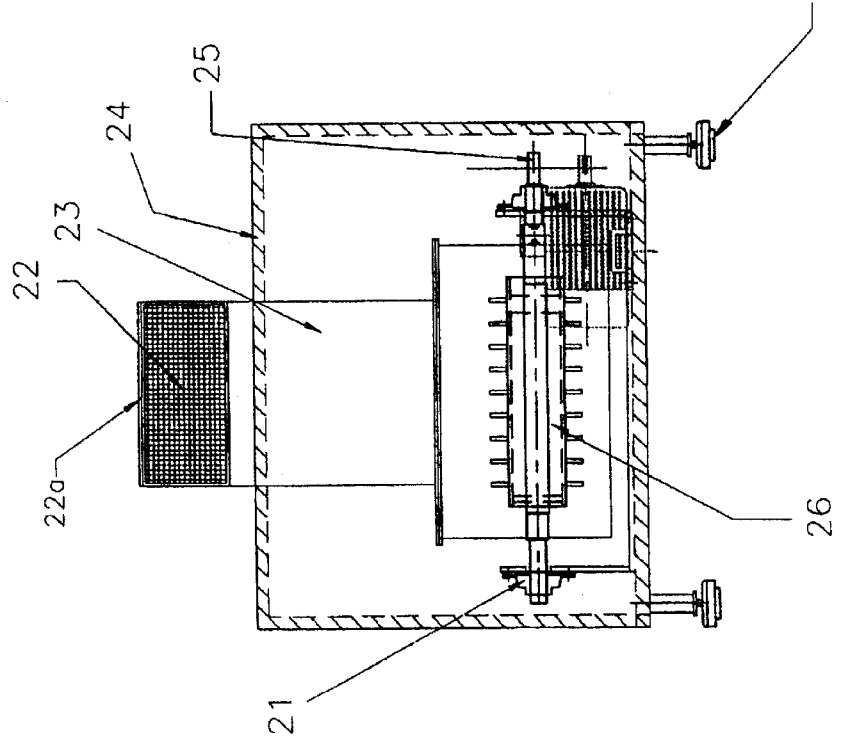
FIG. 2 shows a front view of the crushing mill used in the process of the present invention.

FIG. 2 is a front view of the crushing mill, with the following reference numbers:

21. Self-centering and self-sealing bearings on the central shaft
22. Retractable lid with sealed closure
23. Stainless steel hopper.
24. Soundproof coating.
25. Drive shaft.
26. Rotary mill FIG. 3 shows a side view of the machine, having the following reference numbers:
31. Water and germicide spray nozzles inside the crushing chamber.
32. Flask containing germicidal solution
33. Stainless steel housing
34. Water spray perforated pipe .
34A. Container inlet.
35. Driving belts
36. Driving pulley.
37. Motor.
38. Stationary mills.
39A. Outside connection to sewer system.
39B. Filtering mesh.
39C. Crushing stainless steel chamber.
39D. Manhole cover inlet to the crushing chamber.
39E. Germicidal solution dose pump.
39F. Antivibration supports for the machine.

In a preferred embodiment, the machine is provided with a PLC to execute the automation of the machine's operation and to control all the functions thereof, by receiving signals from end-of-stroke sensors in order to emit, by means of a luminescent-sound operation signal, status signals and failure interruption alarm (not shown in the drawings). In order to keep the cost of the machine as low as possible, the use of a PLC with 4 digital inputs (plus 2 for future use), 3 analog inputs and 8 digital outputs, in order to receive on/off signals from 4 end of stroke sensors has been contemplated. The following failures would thus be detected: a) lack of water in the reservoir, b) mobile mill not running (belt cut or slipping), c) outlet to sewer clogged and d) engine thermal detector actuated by overload. In a preferred embodiment, but without being limited to any specific model or brand, the use of a Honeywell® model DCP 100 PLC, with Honeywell®—Microswitch ® sensors, BZ/BA type and Honeywell® flow switches, model FS4 have been suggested. Programming of the automatic functions of the grinding or crushing machine are not a part of the invention and, in a preferred embodiment, this is carried out in a "ladder" programming, or in any language recommended by the PLC supplier.

In a preferred embodiment, a wash and inner disinfecting dose pump, as well as antivibration supports, to eliminate vibrations that might be transmitted to the floor and/or walls, are also included.

Tests

A detailed description of the tests carried out on the materials used in prototypes is now shown:
Materials: The test container prototypes were made of the following materials:
A) Molded pulp (MP).
B) Molded cardboard (single and double corrugation).
A) Molded Pulp (MP)

Cellulose pulp is a cellulose paste prepared from a mixture of fresh raw materials and recycled material from paper, cardboard, pieces of cloth, etc., from vegetable, organic sources with the addition of chemical or natural substances, plasticizers or binders, and dye pigments or bleaches. This material is known to be used in the manufacture of boxes and trays (so called "maples") for egg packaging, pizza package boxes and similar food products.

A-1) Determination of the Specific Weight Per Area Unit and Density of the Material (Average Values)

Specific Weight per area unit: Usually expressed in g/m2.

Density: Expressed in kg/dm3.

Procedure

Four Templates of equal dimensions are cut with 5 cm×5 cm =25 cm2 (i.e. aprox. 3,9 sq. inches) and weighed on a DPSA brand analytical scale, model 8009 P, with 5½ digit resolution, maximum capacity 1 kg, lowermost graduation 0,1 g and precision ±1 %. The thickness of the chosen samples was of approximately 0.04 inches (1 mm).

Once the samples are taken the following values are obtained:

1. 2.1443 g
2. 2.1565 g
3. 2.1188 g
4. 2.1541 g

Obtained Values:

Specific Weight: 857 g/m2. (0.553 g/ sq. inch)

Density: 0.857 kg/dm3 (14.0 g cu. inch)

A-2) Determination of Longitudinal and Transverse Tear Strength (ELMENDORF Test)

Test apparatus: ELMENDORF (empirical unit in reference scale)

This test is used for paper, cardboard and cellulose-derived materials. The harder the material, the lower the resulting ELMENDORF number.

Test Methodology:

1) Five samples of the material with a thickness of approximately 0.2 inches (5.0 mm) are cut and held with two clamps.
2) The bladed pendulum is released from its upper position, and in its stroke the blades cut the test sample, dragging the reference indicator, which stops, thus indicating an empirical non-dimensional value on the Elmendorf scale.
3) The test is repeated with another batch of samples after which the obtained values are averaged.

Pulp test Results:

longitudinal tear: 40–50 Elmendorf

Transverse tear: 65–75 Elmendorf

A-3) Determination of Stress-strain and Flexural Strength upon the Use of Pressure (Bursting)

This is effected by placing the sample between two ring-shaped clamps and exerting hydraulic pressure through a membrane until either stress or crushing causes the rupture.

The obtained result was: 150–200 lbs/sq. inch.

A-4) Permeability Tests

Several containers in the shape of a truncated cone, having a diameter of 33 mm ±0,5 mm (1.3 inches ±0.02) across the major base, 5 mm ±0,5 mm (0.2 inches ±0.02) across the minor base and a height of 20 mm ±0,5 mm (0.78 inches ±0.02), and a thickness of approximately 1 mm (0.04 inches) were used. Permeability tests on liquids at various initial temperatures were carried out by subjecting the pulp material to the action of water at a level of 7 to 15 mm (0.27 –0.59 inches) over the bottom surface.

The following instruments were used for these tests:

(1) Wet bulb thermometer (Range −10° C. to 110° C.)

(1) 10 ml measuring pipette.

Material tested: plate with areas in the shape of truncated cones.

The temperature variations were measured as a function of time, working at room temperature (R.T.=20° C.), and examining the product's permeability.

Test 1:

Liquid: Water

Volume: 5 ml.

Hliquid: 7 mm (0.27 inches)

Ti=60° C.

R.T.=21° C.

Figure 11:
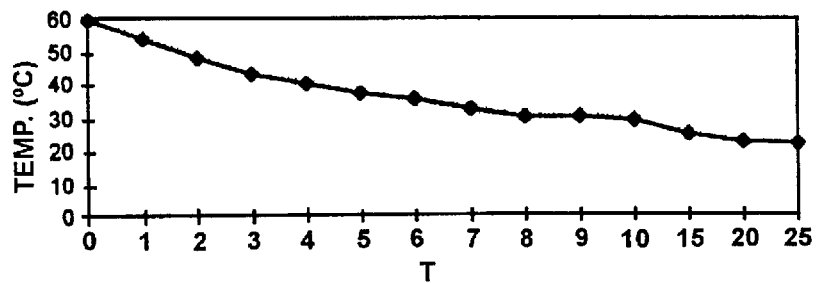
FIGS. 11–14 are temperature charts =f (time) for permeability essays described later.

Variations in the temperature of water for the duration of the test are shown in FIG. 11.

Results: No permeation of humidity was observed.

Test 2:

Liquid: Water

Volume: 10 ml.

Hliquid: 15 mm

Ti=43° C.

R.T.=21° C.

Figure 12:
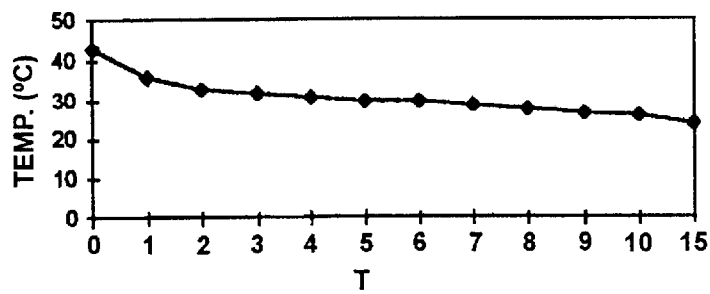

The change in the temperature of water for the duration of the test is shown in FIG. 12.

Results: No permeation of humidity was observed.

Test 3:

Liquid: Water

Volume: 10 ml.

Hliquid: 12 mm

Ti=70° C.

R.T.=21° C.

Figure 13:
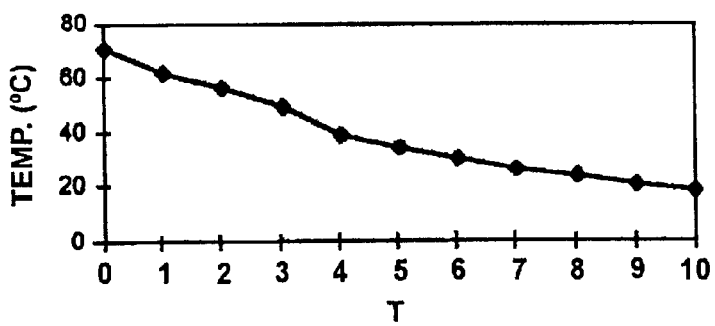

The change in the temperature of water for the duration of the test is shown in FIG. 13.

Results: Some wetness was observed on the walls of the test material.

Test 4:

Liquid: Water

Volume: 10 ml.

Hliquid: 15 mm

Ti=0° C.

R.T.=21° C.

Figure 14:
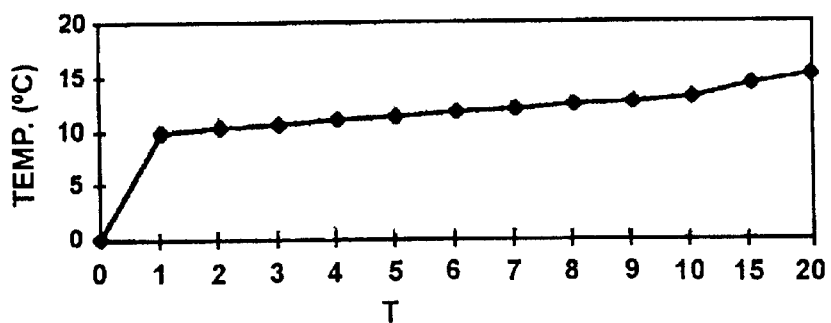

The change in the temperature of water for the duration of the test is shown in FIG. 14.

Test 5:

In order to better resemble the container's structure, samples with different thickness were used.

For a thickness of 1 mm:

Liquid: Water

Volume: 10 ml.

Hliquid: 15 mm

Ti=60° C.

R.T.=21° C.

Figure 15:
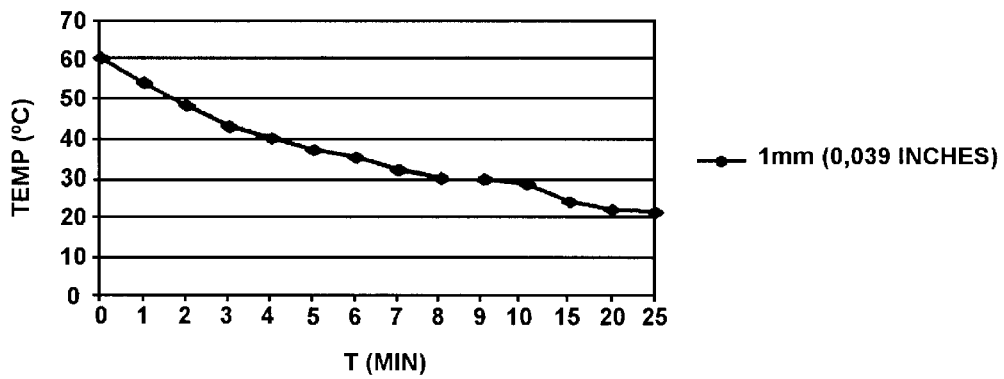
FIGS. 15, 16 and 17 show temperature charts as a function of time (minutes) for permeability tests done on the disposable container embodiments with water at an input temperature of 60° C. (140° F.).

The change in the temperature of water for the duration of the test is shown in FIG. 15.

Test 6:

For a thickness of 2 mm:

Liquid: Water

Volume: 10 ml.

Hliquid: 15 mm

Ti=60° C.

R.T.=21° C.

Figure 16:
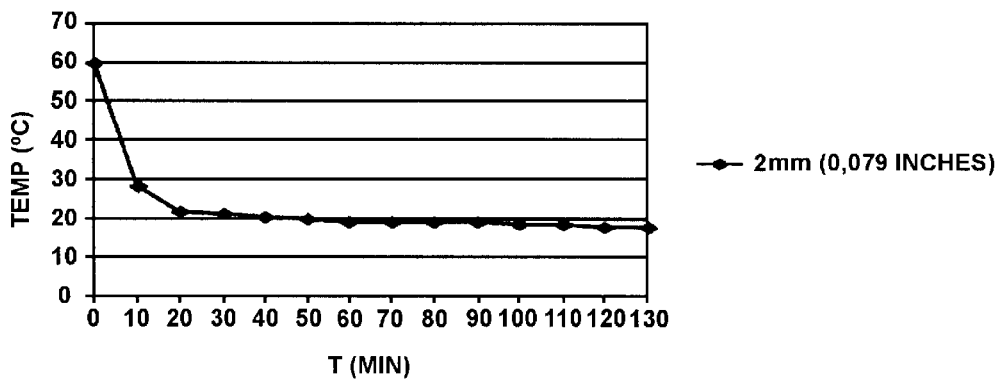

The change in the temperature of water for the duration of the test is shown in FIG. 16.

Test 7:

For a thickness of 5 mm:

Liquid: Water

Volume: 10 ml.

Hliquid: 15 mm $T_i=60°$ C.
R.T.$=21°$ C.

The change in the temperature of water for the duration of the test is shown in FIG. 15.

Results: Temperature decay is very steep during the first 10 minutes and the temperature of the water particularly reaches values under 36° C. after approximately 4 minutes have passed. This quick cooling process benefits the imperviousness of the container Overall Results:

Permeability of the pulp is a reverse function to the temperature of the liquid.

When the temperature of the liquid used is not over 60° C. the material retains its imperviousness without impairment, for a minimum time of 2 hours.

From the tests performed, the only instance wherein humidity was observed on the walls of the material was in Test 3 and this is believed to be due to the high initial temperature of the liquid (70° C.). It is worth noting that human waste liquids are usually at a normal initial temperature of between $T_i \approx 37°$ C. and $T_i \approx 42°$ C. and that, except for highly unusual circumstances, they are not expected to reach the container at a temperature outside this range. Therefore, the temperatures used in the above tests are believed to reflect extreme and more adverse conditions that usual. In addition, the fact that the initial temperature of wastes tends to promptly reach the room temperature favors the imperviousness of the material.

The mentioned cellulose products, once molded to form the cellulose pulp based container, show by themselves imperviousness to the type of liquids that are expected to be present in human feces. The dependency of permeablity to thickness exists but, in these embodiments, variations in thickness may be considered negligible. This is so because the thickness of the container's walls is selected taking in account the structural rigidity needed to withstand a maximum human weight ( approx. 330 lbs.) which exceeds the thickness needed for keeping permeability. Obviously, highly corrosive liquids as for e.g. concentrated acids or alkalis will not be comprised in the scope of the liquids efficiently contained by the invention. For the sake of clarity, further permeability tests have been carried out and it was determined, by means of the same experiments as the ones described above, that the container showed no leaks during approximately 2 hours when replacing water by HCL diluted acid at 50% by weight at 99° F.

Cellulose pulp composition is well known in the art. A great variety of applications have shown that cellulose pulp molded products are useful for permanently containing different types of solid elements and for retaining liquids. In egg tray containers, for example, it is well known that the cellulose pulp will be able to withstand the dampness due to egg breakage without leaking, till the contents finally dries up.

The composition of cellulose pulp used for carrying out the essays, and intended for manufacturing the container is based on:

A) 5–10% ( by weight of the dry fiber mass) of colophone resin, a natural substance of vegetal origin which amalgamates the fibers and gives imperviousness to the final product;

B) 0,5–1% (by weight of the dry fiber mass) of kerosene wax or liquid paraffin suspension, a substance which fills in all the gaps between the fibers, producing therefore a closed and more impervious structure;

C) 0,1–0,5% (by weight of the dry fiber mass) of vegetal coloring matter, due to marketing aspects;

D) 1–10% (by weight of the dry fiber mass) of modified starches for enhancing mechanical strength at high humidity condition;

E) rest of the mixture (complementary %) of cellulose raw or recycled fiber.

Time chosen for Imperviousness

The time selected by the inventor as a minimum for imperviousness should be compatible with the delay that may exist for a nurse to carry out a replacement of the container in a typical health facility, such as a public hospital. A period of 2 hours was considered enough for this circumstance.

Thickness for the Container

As was said above, the thickness for the container was selected taking in account the structural strength needed to withstand a weight of 330 lb. (150 kg). As was said in pages 18–19, the mechanical strength tests were carried out using samples with a thickness of approximately 1.0 mm (0.039 inches) to approximately 5.0 mm (0.197 inches).

Tests were also carried out in order to guarantee the imperviousness of the container when manufactured with a thickness in the range of 0.039 inches to 0.197 inches.

Figure 17:
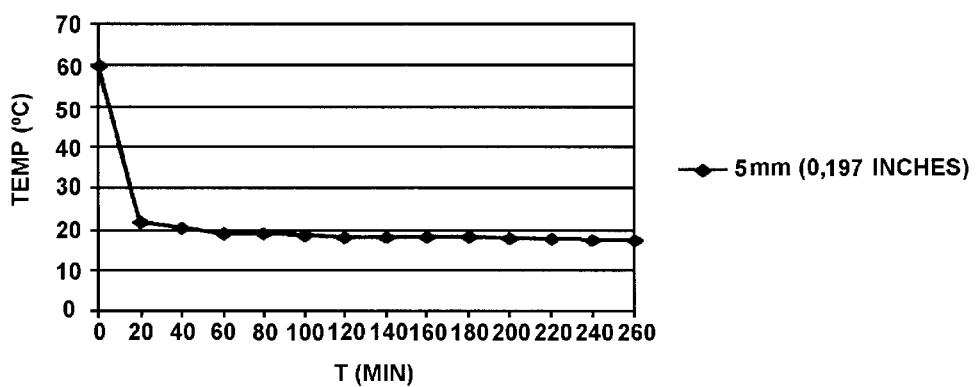

As previously stated, FIGS. 15, 16 and 17 show permeability tests carried out with water at an input temperature of 140° F. (60° C.), which broadly exceeds the temperature of human wastes. As it can be appreciated from these figures, the gradients remain practically constant during the exposure time, with the exception of the first minutes in which a great temperature fall is occurs. ( FIGS. 16 and 17 which correspond to thickness of 0.039 inches and 0.179 inches, respectively). The temperature measurements of the liquid poured into the container during the tests shows a rapidly decreasing logarithmic temperature curve as a function of time. This is favorable and shows that the container is submitted to high temperature only for a very short period of time, thus helping in the imperviousness features. As was mentioned in Test 5, FIGS. 15, 16 and 17 show curves that describe the way liquids rapidly cool off in the container, which particularly benefits the imperviousness feature. For a thickness of 0.079 inches (2.0 mm) the material was able to retain water during a period of time greater than 2 hours in a worst case; and for a thickness of 0.197 inches (5.0 mm) water was kept for more than 3 hours. From the above mentioned tests it can be concluded that the imperviousness of the cellulose walls with a minimum thickness of 2 mm and a maximum thickness of 5 mm, and under the expected temperature and time parameters, complies and even exceeds the requirements, taking in account the intended use.

Based on the previous explanations it should be clear to any skilled person that an impervious cellulose pulp based container, with a thickness of approximately 2 mm ( approximately 0.08 inches) inches may retain water during 2 hours or more and with a thickness of 5 mm (approximately 0.2 inches) water may be retained during 3 hours or more, providing the temperature does not exceed 140° F. It should be noted that the fact that human feces are not entirely formed by water, but include solids and other liquids, is beneficial for the container's ability to retain its contents. Pure water shows lower density and higher surface tension than any impure solid/liquid human feces, causing a stronger capilarity action of the fibers on pure water than on these. That is why the inventor used water in the tests since these reflect a worst case and its results may be extrapolated to any other solid/liquid human feces mixture.

B) Molded Cardboard (MC)

This material is stress-molded cardboard produced under conditions of humidity, temperature and pressure exerted by eccentric-shaft presses, pneumatic presses, electrohydraulic presses or quick presses.

It is a commercially available material, used for building package boxes and other common uses. Depending on the strength that is required, there are two different configurations used for boxes: simple corrugation (low strength) or double corrugation (high strength).

B-1) Determination of Specific Weight and Density of the Material

These assays were not performed because it is a material of common commercial use, with values being published by the suppliers.

B-2) Determination of Longitudinal and Transverse Tear Strength (ELMENDORF test): These tests were not performed because it is a material of common commercial use.

B-3) Determination of Stress-strain and Flexural Strength upon Application of Pressure (Bursting)

No test was performed. The following values were achieved from tables published by suppliers.

Simple corrugation: 40–50 lbs/sq. inch

Double corrugation 180–200 lbs/sq. inch

B-4) Permeability Tests

These tests were not performed because it is a material of common commercial use.

Mechanical Strength Tests Performed on the Disposable Container Made of Cellulose Pulp In the present invention the tensile strength of the assembly for withstanding a user of at least 330 lbs. is achieved by means of two combined features: a) a shell-type lower portion with enough wall thickness and b) a specially designed lid which not only avoids spillage but also contributes in enhancing the stress distribution.

Several tests done on the embodiment samples have shown that the wall thickness for resisting a user of as much as 330 lbs. (150 kg) are in the range of 2 mm ( approx. 0.08 inches) to 5 mm ( approx. 0.2 inches) provided the lid was firmly engaged to the lower portion, thanks to the shell-type shape of the lower portion. This is achieved due to the particular design of the lid which acts as a structural reinforcement for attaining overall resistance of up to 330 lbs.

Figure 18A:
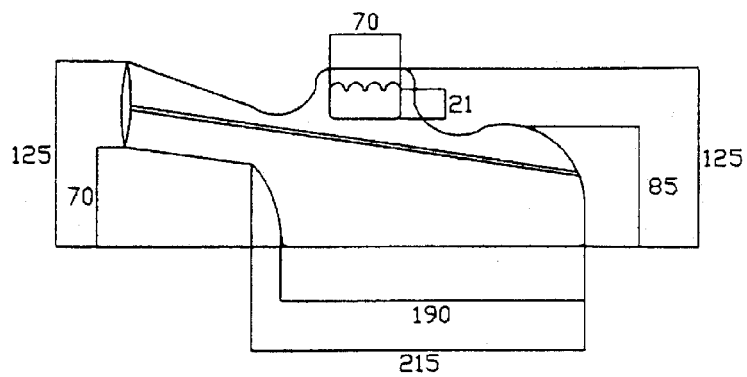
FIG. 18A is a right sideview of the urinal according to the present invention.
Figure 18B:
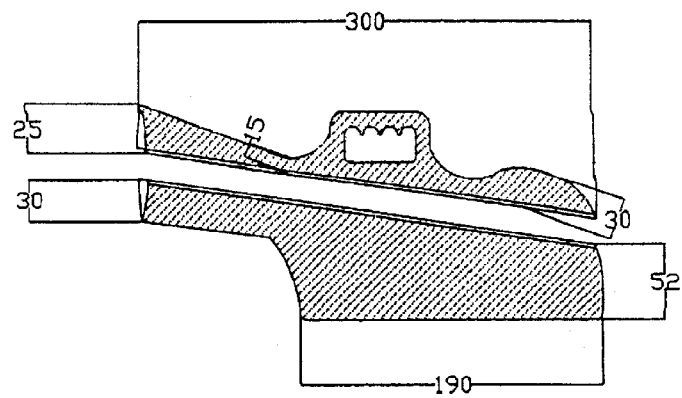
FIG. 18B is a right sideview of the upper and lower portions of the urinal of the present invention.
Figure 18C:
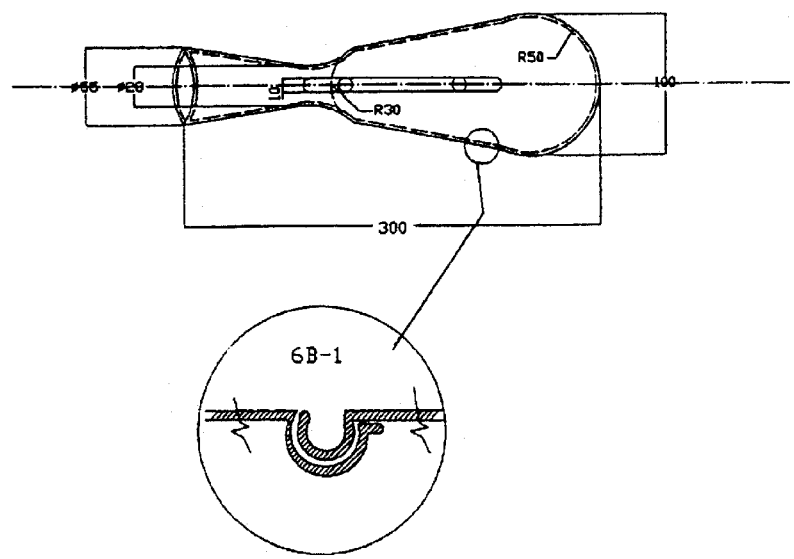
FIG. 18C is a plan view of the lower portion of the urinal of the present invention, showing a detailed view of the snapping engagement flange of the upper and lower portions.

Another important feature of the lid's design and of the upper and lower portions of the container of FIGS. 18A–18C is the particular snap-in flange which allows for a tight engagement. Maximum care was taken in order to obtain a snap in engagement that would resist the patient's maximum weight even under lid or upper portion deformation. Also care was taken to obtain an engagement that would be able to resist the maximum stress without the need of any gluing or binding liquid whatsoever. The addition of glues is highly undesirable since these may affect skin of particularly sensible patients and may affect the biodegradability of the product. The need of using glues for engaging the various parts also creates an undesirable necessity for stocking these products. Test have been carried out in order to confirm that, once the lid was firmly placed, the engagement could withstand the maximum stress of 330 lbs. without letting the lid get loose and without any need of gluing or chemical binding.

Flange Design

As was said before, the upper and lower portions of both container embodiments (the urinal and the bed pot) are designed to be pre-assembled in a last optional step in the manufacturing process or may also be manually assembled right before being used, without the need of any previous training or particular set of instructions.

FIG. 7C shows the engagement disposed around the lid and the lower portion in the bedpan embodiment and FIG. 7B shows an enlarged view of the engagement 71A. FIG. 18C shows the snap-in flange engagement in the urinal embodiment, with an enlarged view 6B-1. Tight engagement is achieved thanks to a male flange and a female flange which snap one into the other, a technique which is well known in cardboard-made boxes and the like. However, in this particular case, both flanges were carefully dimensioned in order to obtain a swift snap-in, but at the same time, strong engagement for withstanding a patient of up to 330 lbs. weight. The male flange is 5 mm thick and follows a substantially circular design of 7 mm radius. The female flange is also 5 mm thick, substantially circular, and with a 12 mm radius. The horizontal snap-in design allows for applying pressure on both portions and minimizes any possibility of lid opening during usage.

Container Surface Design

Since the bedpan contacts the patient's body, it is of great importance that it offers a non-slipping surface in order to avoid undesired slippage of the container assembly out of its useful position. Therefore the outer surface of the bedpan is also designed to fulfill these requirements, by means of a texturized, anti-slipping surface which is obtained thanks to the particular annealed mesh finish of the mold used to produce the container. In the urinal embodiment, due to its different usage, the anti-slippage outer surface finish is also used in order to allow using the same molding technique and for providing comfortable contact with the patient's skin. The same surface finish is also used in the inner surface of the urinal and particularly in the area where the cellulose pulp gets in contact with the male patient's skin. The mold for obtaining this particular surface finish is described in the paragraphs referred to the manufacturing process.

Figure 6A:
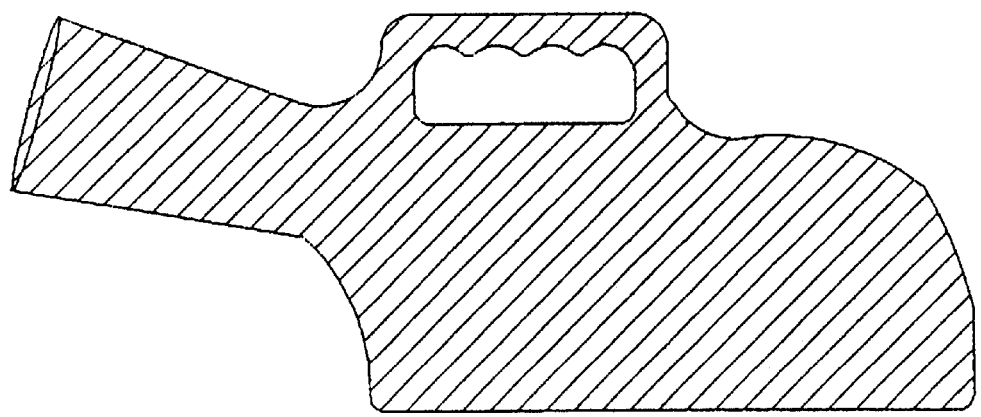
FIG. 6A is a side view of the disposable container embodiment in the shape of a urinal for male patients.
Figure 6B:
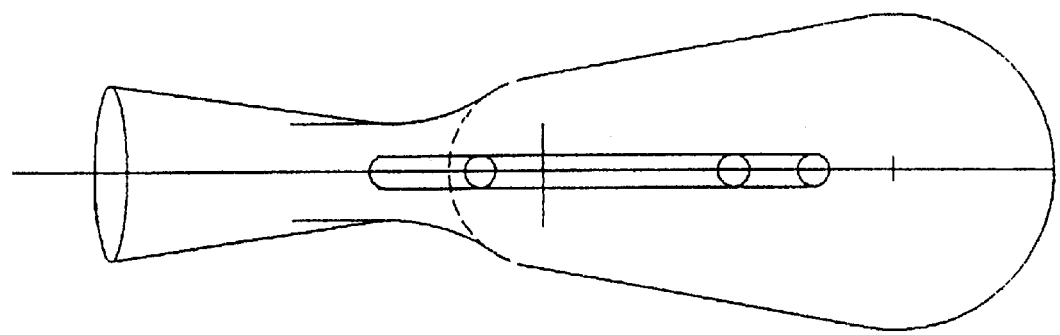
FIG. 6B is a plan view of the disposable container embodiment in the shape of a urinal for male patients.

Flat bed-pot prototypes were made of cellulose pulp (FIG. 6B), with the insertion of nerves or ribs to prevent the product from collapsing under stress loads higher than the maximum weight of 150 kg (330 lbs.) pertaining to a human being sitting over it under conditions of use.

A weight of 150 kg (330 lbs.) was considered to be equivalent to a person sitting on the flat bed-pot, spreading some of his or her legs and buttocks' weight outside the same (mattress, side pillows, chairs, floor, etc.). The weight used is higher than the average weight of a person and it also takes into account the additional stress from the dynamic application of the load, for the user will bear on the container with a certain drive. The force was applied by means of a fixed hand press and it was monitored by means of a dynamometer. The application time was of 30 minutes, non-stop.

Load test results

On performing the test, its stress rigidity was considered as satisfactory. When exposed to loads, slight plastic strains were observed, which did not preclude the use of the container, retaining the volume thereof as a liquid receptor on tilting the flat bed-pot during handling. No cracks, ruptures or tears in the material were detected, the container thus retaining its impervious character.

Rib arrangement

In a preferred embodiment, the insertion of reinforcing ribs is considered in order to insure the structural rigidity of the container upon impacts and maximum use. The ribs

- may or may not be aligned with the symmetric axis of the product;
- may be a part of the contour in a radial arrangement that restricts the volume thereof;
- plugs may be added in the area of the liquid receiving pail, their arrangement remaining parallel to the volumetric boundaries; or may be placed inside or outside, and of the same material or one that is easy to crush or biodegradable.

Use of Deodorant Additives in the Disposable Container

In a preferred embodiment it is desirable to use deodorant products that do not imply a considerable increase in cost but which do upgrade the product. Pads (multilayer material soaked in scented substances) are used in the polyethylene or polypropylene preserving bags comprising the aseptic packaging of the product. The pad must be stable until use; it may preferably comprise a removable label that peels off on withdrawing the preserving bag, with the scent or deodorant remaining in the adhesive thereof.

Experiments for Testing the Crushing of the Container

These were carried out on an experimental model of crushing machine. The following results were achieved:

Number of containers broken down per minute =3 to 5.

Amount of wash water used per cycle =5 to 10 I.

Amount of germicide and/or disinfectant used per cycle =10 ml.

Motor power =2 to 3 HP

Particulate material =10 to 12 mm mesh.

Precautions taken During Transfer of Containers:

In a preferred embodiment, it is contemplated to effect the collection of containers used in clinics, hospital wards, nursing homes, etc., with the help of a transfer carriage wherein the containers are carefully stored, preferably within their preserving bag until they are crushed by the crushing mill and optionally without using such bag.

Features of the transfer carriage

1. Minimum gage, about 600 mm (23.6 inches)
2. Smooth rolling (wheels with polyurethane treads and bands)
3. Stainless steel plate housing with container storage areas.
4. It should not have areas and/or sectors which make cleaning and disinfection difficult.
5. Sliding door openings to facilitate their opening in narrow hallways.
6. Drawbar on side of the two turning wheels.

The invention claimed is:

1. A container for collecting human wastes, comprising:

an upper portion and a lower portion, said container being integrally made of a disposable, substantially biodegradable, grindable material, said material comprising cellulose pulp and being completely grindable by a grinding, liquefying and deodorizing machine for dumping said disposable material through a sewer system;

said upper and lower portions having a texturized anti-slipping finish integrally embedded on the outer surface of the material, said finish corresponding to a grid pattern;

said upper and lower portions including corresponding snap-in peripheral engaging flanges provided thereon for engaging one of said upper and lower portions to the other without the use of gluing products;

said lower portion having an opening therein such that when said upper portion is snapped into said lower portion, said upper portion extends only partially around a perimeter of said opening; and said snap-in peripheral engaging flanges providing sealed engagement of said upper and lower portions when subjected to weight stress by a patient.

2. The container according to claim 1, wherein the container is a bedpan.

3. The container according to claim 2, wherein said cellulose pulp is formed by 5 to 10% of colophone resin, 0.5 to 1% of kerosene wax or liquid paraffin suspension, 0.1 to 0.5% of vegetal coloring matter, 1 to 10% of modified starches, and the rest cellulose raw or recycled fiber, all percentages being weight percentages of a dry fiber mass.

4. The container according to claim 2, wherein said grid pattern corresponds to a mesh openness of grade #50 to #60.

5. The container of claim 2, wherein the flanges define male and female flanges which are substantially circular.

6. The container of claim 5, wherein the male and female flanges each have a thickness of 5 mm.

7. The container of claim 5, wherein the male flange has a radius of 7 mm.

8. The container of claim 5, wherein the female flange has a radius of 12 mm.

* * * * *